United States Patent
Bluecher et al.

(10) Patent No.: US 11,559,367 B2
(45) Date of Patent: *Jan. 24, 2023

(54) WENZEL-CASSIE GLOVE

(71) Applicant: BVW Holding AG, Cham (CH)

(72) Inventors: Lukas Bluecher, Eurasberg (DE); Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 314 days.

This patent is subject to a terminal disclaimer.

(21) Appl. No.: 16/557,519

(22) Filed: Aug. 30, 2019

(65) Prior Publication Data
US 2019/0388170 A1    Dec. 26, 2019

Related U.S. Application Data

(63) Continuation of application No. 15/616,919, filed on Jun. 8, 2017, now Pat. No. 10,433,924, which is a
(Continued)

(51) Int. Cl.
*A41D 19/015* (2006.01)
*A61B 42/10* (2016.01)
(Continued)

(52) U.S. Cl.
CPC .......... *A61B 42/10* (2016.02); *A41D 19/0003* (2013.01); *A41D 19/0082* (2013.01);
(Continued)

(58) Field of Classification Search
CPC .......... A41D 19/0062; A41D 19/01564; A41D 19/01558; A41D 2400/80; A61B 42/10; A61B 42/00
See application file for complete search history.

(56) References Cited

U.S. PATENT DOCUMENTS 2,049,323 A    7/1936 Schmidt
5,792,531 A    8/1998 Littleton et al.
(Continued)

FOREIGN PATENT DOCUMENTS

CN    1897906    1/2007

*Primary Examiner* — Tajash D Patel
(74) *Attorney, Agent, or Firm* — Patterson Intellectual Property Law, P.C.; Ryan D. Levy; Mark A. Kilgore

(57) ABSTRACT

A glove with an enhanced gripping textured surface is disclosed herein. In preferred embodiments, the glove contains a palm region adapted to cover the palm of a person's hand, a thumb region extending outwardly from the palm region, an index finger region disposed adjacent the thumb region, a middle finger region adjacent the index finger region, a ring finger region adjacent the middle finger region, and a little finger region adjacent the ring finger region with each region containing a textured surface. In preferred embodiments, the textured surface is formed by a plurality of dimensionally hierarchical structures superimposed in layers. The textured surface of the invention, when in contact with wet tissue, repels water at a first texture layer and traps tissue at a second texture layer, such that when in tissue contact, especially exudative tissue, tissue fixatively localizes to the glove surface.

14 Claims, 10 Drawing Sheets

Related U.S. Application Data continuation-in-part of application No. 15/285,529, filed on Oct. 5, 2016, now Pat. No. 10,259,558.

(60) Provisional application No. 62/347,070, filed on Jun. 7, 2016.

(51) Int. Cl.
| | | |
|---|---|---|
| *A61B 42/00* | (2016.01) | |
| *A41D 31/12* | (2019.01) | |
| *A41D 19/00* | (2006.01) | |

(52) U.S. Cl.
CPC . *A41D 19/01547* (2013.01); *A41D 19/01558* (2013.01); *A41D 31/12* (2019.02); *A61B 42/00* (2016.02); *A41D 19/0062* (2013.01); *A41D 2400/80* (2013.01)

(56) References Cited

U.S. PATENT DOCUMENTS

| | | |
|---|---|---|
| 6,035,444 A | 3/2000 | McGrew |
| 6,081,928 A | 7/2000 | Bourne |
| 7,771,644 B2 | 8/2010 | Flather et al. |
| 9,120,670 B2 | 9/2015 | Hulseman et al. |
| 9,908,274 B2 | 3/2018 | Hulseman et al. |
| 9,988,201 B2 | 6/2018 | Darin et al. |
| 10,377,044 B2 | 8/2019 | Hulseman et al. |
| 10,433,924 B2 * | 10/2019 | Bluecher ................ A61B 42/00 |
| 10,458,053 B2 | 10/2019 | Hulseman et al. |
| 10,575,667 B2 | 3/2020 | Hulseman et al. |
| 10,687,642 B2 | 6/2020 | Hulseman et al. |
| 10,825,710 B2 * | 11/2020 | Lee ..................... H01L 23/3121 |
| 10,889,005 B2 | 1/2021 | Hulseman et al. |
| 2005/0148984 A1 | 7/2005 | Lindsay et al. |
| 2006/0150300 A1 | 7/2006 | Hassan et al. |
| 2007/0199130 A1 | 8/2007 | Gray |
| 2010/0011484 A1 | 1/2010 | Williams |
| 2010/0028604 A1 | 2/2010 | Bhushan |
| 2014/0276407 A1 | 9/2014 | Devries |
| 2015/0143609 A1 * | 5/2015 | Francisco Costa .......... A41D 19/0006 2/167 |
| 2015/0272242 A1 | 10/2015 | Bevier |
| 2015/0359277 A1 | 12/2015 | Todorov et al. |
| 2015/0368838 A1 | 12/2015 | Hulseman et al. |
| 2017/0014111 A1 | 1/2017 | Hulseman et al. |
| 2019/0062155 A1 | 2/2019 | Hulseman et al. |
| 2020/0338808 A1 | 10/2020 | Hulseman et al. |
| 2021/0086371 A1 | 3/2021 | Hulseman et al. |
| 2021/0127635 A1 * | 5/2021 | Michaelson ............ B29C 45/16 |

* cited by examiner

WENZEL-CASSIE GLOVE

RELATED APPLICATIONS

This application is a continuation of U.S. application Ser. No. 15/616,919 filed on Jun. 8, 2017, which claims the benefit of U.S. provisional application No. 62/347,070 filed on Jun. 7, 2016, and which is a continuation in part of U.S. application Ser. No. 15/258,529 filed on Oct. 5, 2016 which claimed the benefit of U.S. provisional application No. 62/237,460 filed on Oct. 5, 2015, the contents of which are hereby incorporated by reference in their entirety.

TECHNICAL FIELD

The present invention relates to the field of medical. More specifically, the invention relates to grip-enhanced textured gloves for use in surgical procedures. Gloves of the present invention are generally comprising moldable, elastomeric polymers such as nitrile, latex, polyurethane and the like.

BACKGROUND

A wide variety of gloves with enhanced exterior gripping surfaces have been designed and used over the past century. The following describes patents and/or publications which are related to the Applicant's inventive concept. For example, U.S. Pat. No. 4,038,787 discloses a glove having a flexible body with a plurality of discrete abrading units disposed on the glove to permit free flexing of the finger stalls, the thumb and palm. The abrading units comprise a plurality of hard and sharp particles such as silicon carbide dispersed in an adhesive. The abrading units are fixedly connected to the glove surface by a waterproof adhesive.

U.S. Pat. No. 4,218,778 designed a highly stretchable surgical glove which discloses an oval structure from front-to-back at the mid joint area of the wearer's fingers, and a side-to-side ovaling of the glove portion near the mid point of the wearer's fingernail. Thereby it is claimed that the glove has added flexibility and tactile sensitivity at the tip section of the glove's fingers.

U.S. Pat. No. 4,658,444 shows an improved surgical glove that contains a smooth latex skin coated onto the front surface of the glove so that surgical tape will not stick thereto. A textured contoured flap is pivotably secured to tips of the finger portions of the glove while another textured contoured flap is pivotably secured to the tip of the thumb portion of the glove so that the wearer can increase their grip to hold various items.

U.S. Pat. No. 6,640,341 discloses single and two-sided hand and finger thimbles constructed to mount over the fingertips to provide non-slip gripping surfaces and improved protection at the fingertips and palm. Several thimbles include surfaces that contain impenetrable shields, elastomer pads, or raised patterns of a coated elastomer.

US patent application publication 2008/0235850 features a "hand covering" comprising a gripping region of mesh material having a first permeability and a first coefficient of friction. Regions of the hand covered by other than the gripping region are covered by a different material having a second coefficient of friction lower than the first and a second permeability lower than the first permeability.

US publication 2010/0011484 discloses knit fabric gloves having grip/protective members, and also describes a process of manufacturing same. One embodiment comprises depositing an adhesive onto a backside of a sheet of grip/protective material, and fusing the adhesive to the backside of the sheet of grip/protective material using a heat/pressure procedure.

Surgical gloves typically comprise a smooth exterior, or they may comprise texturing that attempts to increase the grip or frictional resistance of the glove when interacting with objects. Smooth exterior elastomeric gloves are often inadequate for manipulating wet or otherwise slippery objects. Existing textured gloves are known to inhibit or decrease tactile feedback to the user. With reduced tactile feedback, users are prone to have difficulty manipulating slippery objects, such as organs, which may result in tissue injury.

Another drawback common to textured gloves is a reduced flexing ability. Frequently, in order to apply texturing, additional material must be applied to the glove. The additional material can make these gloves stiff and hard to flex thereby decreasing the dexterity of a gloved hand. Likewise, with reduced dexterity, users are also prone to have difficulty manipulating slippery objects which may also result in tissue injury.

In order to limit the amount of material that is added to the glove for texturing, many textured gloves consist of texturing on one side of the glove resulting in the glove being hand specific. The hand specific factor limits the longevity and the usage of these gloves such as in the event of one glove getting damaged which automatically renders the other glove of the pair as unusable, since each glove is hand specific.

Due to these drawbacks, the lack of strong grip in the various gloves presently being used often makes a user vulnerable to fatigue during prolonged glove usage common during surgeries. The lack of firm grip makes the tissue grasping less precise and controllable while being held in the hands and thus results in unnecessary tissue damage and an uncomfortable work environment.

BRIEF SUMMARY

The present disclosure provides gloves having a hierarchically textured surface that reversibly adheres to living tissue, such as organs, encountered during surgical procedures. These surfaces create a non-slip contact with tissue that does not require a substantial normal force to establish grip. Reduced normal force reduces user fatigue and tissue damage A scale of interaction is defined by the surface texture of the present gloves, and is typically hierarchical, and characterized by at least two spatial scales, one on the order of 100 to 1000 micrometers (microns) and another on the order of 10 to 100 microns. The surface texture may induce one state with a large difference between preceding and receding contact angles (contact angle hysteresis), or alternatively another state with a small contact angle hysteresis. States of interest are known respectively as Wenzel and Cassie states. Each of the hierarchical spatial scales may induce separately a Wenzel or Cassie state, such that combinations are possible on a multiplicity of spatial scales. It is this combination of states that results in the surprising and advantageous non-traumatic gripping feature of the present gloves.

These states are phenomena between hydrophobic and hydrophilic components of a mixture residing at a tissue surface interface. In the Cassie state the glove is resistant to hydrophobic debris adhesion, for example oil in an oil water mixture. In the Wenzel state the implant is reversibly adherent to a hydrophilic surface, for example an organ surface. In hybrid Cassie-Wenzel states, where one texture scale is Wenzel and the other is Cassie, the adherent glove surface can be both localizing to a wet surface and resistant to hydrophobic contaminants such as oil.

The interaction of a solid textured surface with water in a gaseous environment is described by the Cassie-Baxter model. In this model, air is trapped in the microgrooves of a textured surface and water droplets rest on a compound surface comprising air and the tops of micro-protrusions. However, regardless of the material (organic or inorganic) used and geometric structure of the surface texture (particles, rod arrays, or pores), multiple scales of texture in combination with low surface energy has been required to obtain the so called superhydrophobic surfaces. Superhydrophobicity is variously reported as a material exhibiting a contact angle with water that is greater than contact angles achievable with smooth but strongly hydrophobic materials. The consensus for the minimum contact angle for a superhydrophobic substance is 150 degrees, so in this context most of the embodiments of the present invention are not strictly superhydrophobic, although this option is not excluded. The reason for this is that a Wenzel-Cassie state lies in its hydrophobicity between non-textured surfaces and surface that generate a Cassie-Baxter interface. In optimizing the adherence of the gloves of the present invention superhydrophobicity is just one aspect of a number of interesting texture controlled mechanisms, and in this context the contact angle is less important than the contact angle hysteresis.

A hydrophobic surface repels water. The hydrophobicity of a surface can be measured, for example, by determining the contact angle of a drop of water on a surface. The contact angle can be measured in a static state or in a dynamic state. A dynamic contact angle measurement can include determining an advancing contact angle or a receding contact angle with respect to an adherent species such as a water drop. A hydrophobic surface having a small difference between advancing and receding contact angles (i.e., low contact angle hysteresis) results in surfaces with low resistance to in plane translation (low adherence). Water can travel across a surface having low contact angle hysteresis more readily than across a surface having a high contact angle hysteresis, thus the magnitude of the contact angle hysteresis can be equated with the amount of energy needed to move a substance.

The high surface area is achieved by superimposing multiple structures one on top of the other in superposition. When these multiple structures are sufficiently different in dimension then the superposition of these structures is referred to as a hierarchical structure or pattern. A subset of surfaces useful in the present invention are characterized as superhydrophobic.

A hydrophobic/hydrophilic contact mixture is a liquid/solid mixture or liquid/gas mixture in which first component of solid, liquid or gas is more hydrophilic than the second component of solid, liquid or gas.

In particular the present invention relates to elastomeric gloves having at least part of their surface coated with a thin, well adherent, porous or nonporous coating with super hydrophobic properties. The static water contact angle values, measured on a smooth and plane surface, is higher than about 120', preferably higher than 130°, more preferably higher than 150°.

When organic synthetic resins are chosen, such substrate materials could be fabricated from polyethylene, polyacrylics, polypropylene, polyvinyl chloride, polyamides, polystyrene, polyurethanes, polyfluorocarbons, polyesters, silicone rubber, hydrocarbon rubbers, polycarbonates and other synthetic polymers. A particularly preferred polymeric substrate is polyethylene or polypropylene as used e.g. in the manufacture of nonwoven textile substrates.

In seeking to produce texture on the surface of a single dip polymeric glove by a texture structure found at the surface of the dipping glove-former, it is extremely difficult to produce a glove that has good grip while being reliably formed without holes. It has now been unexpectedly found that good grip can be obtained by the superposition of hierarchical structures, the largest of which is sinusoidal, on which the polymeric dip solution spreads uniformly and generates a layer of substantially uniform thickness without pooling. By virtue of the hierarchical structure, adhesive texture is established without the need for deposition of extra material on a substantially flat surface, thereby texture is achieved in the present invention without substantial thickening the glove.

It is an object of the present invention to provide textured gloves that do not inhibit or decrease tactile feedback to the user.

It is an additional object of the present invention to provide a textured glove with uncompromised tactile feedback to provide for the manipulation of slippery objects, such as organs, which do not cause tissue injury Another object is to provide textured gloves uncompromised in flexing ability.

Accordingly, it is another object to provide ambidextrous gloves, with the texture on two sides of the glove, or over the entire glove surface, without limiting glove flexibility.

It is a further object to provide surgical gloves with reduced fatigue aspects beneficial during prolonged glove usage common during surgeries.

In some embodiments, the present disclosure provides a medical glove comprising first and second sides, four finger enclosures including four fingertip portions, a thumb enclosure including a thumb tip portion, a palm area on the first side, a backhand area on the second side, and a wrist portion, wherein at a least a portion of the glove comprises a hierarchically surface texture comprising first and second microstructures, wherein a the second microstructures are smaller than the first microstructures, and a plurality of the second microstructures is disposed on each of the first microstructures.

The hierarchical surface texture may, in some embodiments, further comprise a third microstructure, wherein the third microstructure is smaller than the second microstructure, and a plurality of the third microstructures are disposed on each of the second microstructures.

The hierarchical surface texture is can be disposed on at least one finger portion, the thumb portion, the palm area, or a combination thereof. The texture may be arranged in a variety of advantageous patterns on the fingers, fingertips, palm areas, thumbs and provide as circular or oval shapes, dots, squares, or other geometric configuration depending on the particular needs of the user.

Furthermore, the hierarchical surface texture can be provided on both the first and second sides of the glove. In such embodiments, the gloves are ambidextrous.

In some embodiments, the first microstructure has a size ranging from 25 microns to 1000 microns, the second microstructure has a size ranging from 5 microns to up to 100 microns, and the third microstructure has a size ranging from 0.5 to up to 10 microns.

In some embodiments, the first microstructure has a height ranging from 100 microns to 1000 microns, the second microstructure has a height ranging from 10 microns to up to 100 microns and the third microstructure has a height ranging from 1 microns to up to 10 microns.

In some embodiments, the first microstructure has a pitch ranging from 100 to 1000 microns, the second microstructure has pitch ranging from 10 micron up to 100 micron, and the third microstructure has a pitch ranging from 1 micron up to 10 microns.

The surface texture may further comprise a fourth microstructure. A plurality the fourth microstructures can be disposed on each of the second microstructures.

The microstructures can have a variety of shapes. For example, in some embodiments, the microstructures are pillars, sinusoids (e.g., 2D sinusoids), flutes, ribs or a combination thereof. Pillars may be cylindrical, square, rectangular, or oval.

In particular embodiments, the second microstructures are cylindrical pillars and the fourth microstructures are flutes or ribs.

In some embodiments, the hierarchical surface texture is imprinted in the glove, while in other embodiments, the hierarchical surface texture is adhesively disposed on the glove.

In some embodiments, the surface area of the hierarchical surface texture is at least twice the area of a smooth plane of the same dimensions. In other embodiments, the surface area of the hierarchical surface texture is at least three, four or five times the surface area of a smooth plane of the same dimensions.

The hierarchical surface texture provides advantageous properties to the medical gloves of the present disclosure. For example, the surface texture in some embodiments forms a reversible adhesion with a mammalian tissue when shear stress exceeds normal pressure, and the textured surface has a static hydrophilic contact angle higher than about 120° and a hydrophobic contact angle lower than about 120°.

In other embodiments, the hierarchical surface texture forms a reversible adhesion with a mammalian tissue when shear stress exceeds normal pressure, and the surface texture has a contact hysteresis angle greater than 5 degrees.

In still further embodiments, wherein the hierarchical surface pattern forms an interface with mammalian bodily fluids, wherein the interface is 1) superhydrophobic, 2) Wenzel-Cassie, or 3) Cassie-Baxter.

DETAILED DESCRIPTION OF THE INVENTION

Figure 1A:
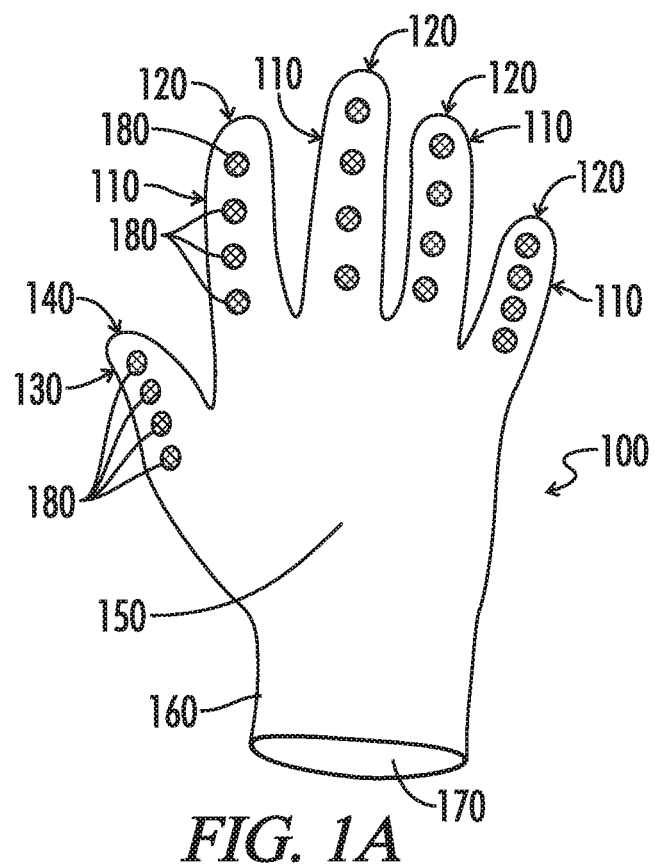
FIGS. 1A and 1B depicts a drawing of a glove having portions comprising a hierarchically textured surface.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that must be included in all embodiments, unless otherwise stated.

The present invention relates to gloves with surfaces comprising textures that initially create Cassie and Wenzel states when exposed to an aqueous environment comprising a hydrophobic component (also referred to herein as a hydrophobic/hydrophilic mixture). The hydrophobic component comprise lipids present in tissues and bodily fluids, or a gas such as ambient air. The Cassie and Wenzel states form as a result of an interface between hydrophobic/hydrophilic mixture and the hierarchical surface texture.

Figure 1B:
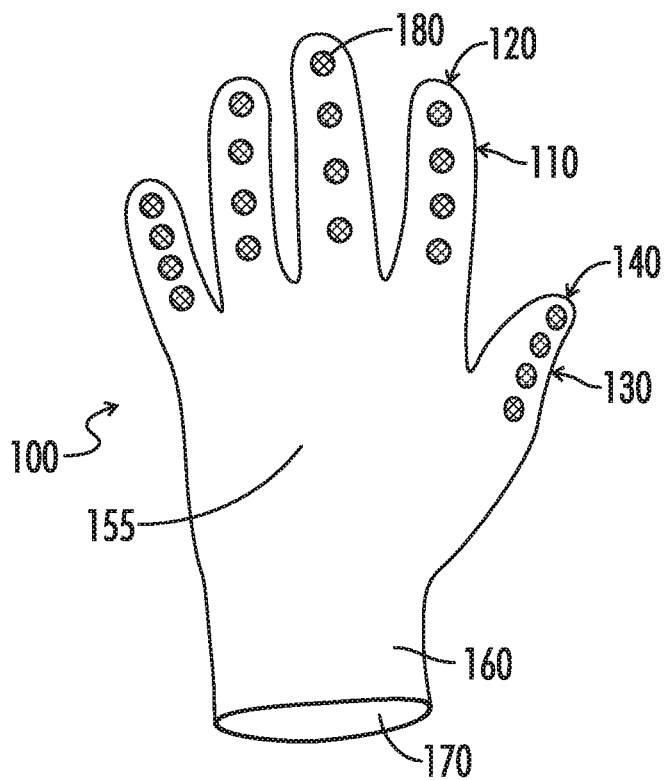

FIGS. 1A and 1B depict first and second sides, respectively, of a medical glove 100 of the present disclosure. The glove comprises finger enclosures 11 and fingertip regions 120, thumb enclosures 130 and thumb tip regions 140, a palm area 150, a back area 155, a wrist area 160 and an opening 170. The glove comprises areas with the hierarchical surface texture described herein. In FIGS. 1A and AB, the surface texture is disposed in a plurality of dots 180 along the finger and thumb enclosures. FIGS. 1A and 1B depict identical surface textures on both sides of the glove, thereby providing an ambidextrous glove. In other embodiments, the surface texture is on only one side of the glove. In still other embodiments, the front and back of the gloves may comprise different arrangements of the surface textures so that the gloves are not ambidextrous.

Figure 2:
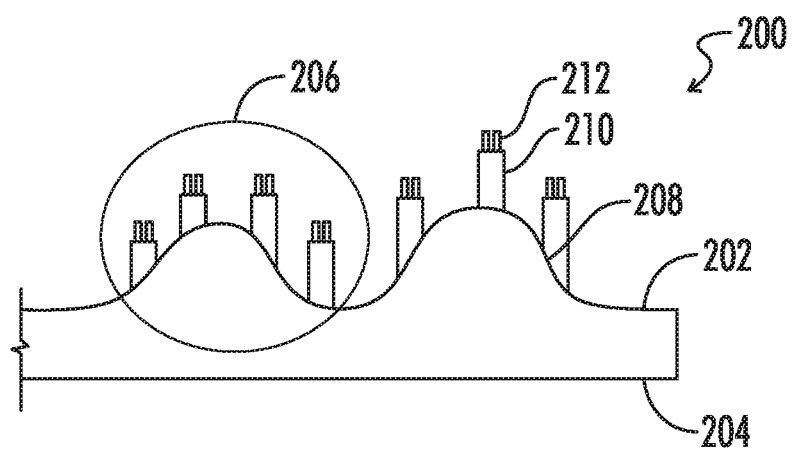
FIG. 2 Depicts a hierarchical surface texture interacting with a droplet of water to form a Cassie-Wenzel state.

Referring now to FIG. 2, generally a surface 200 of the present invention possesses a hierarchical surface 106 comprising a large scale structure with a plurality of protuberances and depressions disposed in a geometric pattern on at least one surface of a substrate 108, and a medium scale structure 210 disposed on at least one surface of the large scale level structure 108 is comprising protuberances 212. The small scale structure 214 is similarly comprising protuberances 216 and depressions 218 disposed on the medium scale structure 210. The large scale protuberances 208 should be high enough so that a hydrophilic component of a hydrophobic/hydrophilic contact mixture does not touch the large scale depressions between adjacent protuberances 208. In the embodiment of FIG. 2, the large scale protuberances 208 may comprise a height H of between about 25 to about 1000 microns and a diameter D of between about 25 to about 2000 microns, wherein the fraction of the surface area of the substrate 208 covered by the protuberances 204 may range from between about 0.1 to about 1.0. The medium scale protuberances 210 may comprise a height 220 of between 5 to about 25 microns and a diameter 222 of between 5 to about 50 microns, wherein the fraction of the surface area of the substrate 208 covered by the protuberances 210 may range from between about 0.1 to about 0.9. The small scale structure 212 may be disposed primarily on the medium scale structure 210. In some embodiments, the first microstructures have a height ranging from 100 microns to 1000 microns, the second microstructure has a height ranging from 10 microns to up to 100 microns and the third microstructure has a height ranging from 1 microns to up to 10 microns. In other embodiments, the first microstructure has a height ranging from 100 microns to 1000 microns, the second microstructure has a height ranging from 10 microns to up to 100 microns and the third microstructure has a height ranging from 1 microns to up to 10 microns In some embodiments, the first microstructure has a size ranging from 25 microns to 1000 microns, 50 microns to 1000 microns, or 100 microns to 1000 microns. In some embodiments, the second microstructure has a size ranging from 5 microns to up to 100 microns, 5 microns to 50 microns, 10 microns to 50 microns or 10 microns up to 100 microns. In some embodiments, the third microstructure has a size ranging from 0.5 microns to up to 10 microns, 0.5 microns to 5 microns, 1 micron to 5 microns, or 1 micron up to 10 microns.

In some embodiments, the first microstructure has a pitch ranging from 100 to 1000 microns, the second microstructure has pitch ranging from 10 micron up to 100 micron, and the third microstructure has a pitch ranging from 1 micron up to 10 microns.

The hierarchical surface structures may have a symmetrical pattern or may be asymmetric, with slightly varying pitches, heights and widths of the microfeatures. The arrangement of hierarchical structures may be geometric and describable generally with a mathematical equation. Alternatively, the hierarchical structures may be randomly disposed, possibly with varying pitch, which is more typical of natural structures. The arrangement of hierarchical structure can generally be described by a fractal dimension. A fractal dimension is a statistical quantity that gives an indication of how completely a collection of structures appears to fill space, in the present case a plane, as one examines that structure on a multiplicity of spatial scales. Specifying a fractal dimension, which is statistical in nature, does not necessarily indicate that the hierarchical structure is well defined by a mathematical equation. Generally, a random arrangement of structures within a specific scale possesses a higher fractal dimension than one in which the structure is mathematically described at all points on a surface. Thus, a random structure may possess an advantage in the aspect that a adhesive surface of the present invention has greater utility when interacting with a natural surface. A higher fractal dimension within a specific spatial scale may be achieved by applying to a substrate multiple pitch arrangements. The protuberances and depressions may be locally scaled with respect to the local pitch. Accordingly, the pitch may vary within a scale structure. In the practical realization of higher fractal dimension structures, the variation of the pitch may be describable by a mathematical equation, for example, a sinusoidal variation of pitch, which would have utility in mimicking natural surfaces.

Generally, structures can be described as sharp-edged or rounded, and this feature is not typically captured by a fractal dimension. Another structural aspect not addressed by the above descriptive parameters is the degree of communication between structures. By communication, it is meant that a structure, such as a protuberance or a depression, has a spatial extent greater than the pitch. For example, a valley surrounding a protuberance may be connected to another valley surrounding another protuberance, thus the depressions are said to be communicating whereas the protuberances are not. The communication may range from 1 to about 1000, more particularly the communication may extend over the entire surface of the substrate.

These structures are constructed with the purpose of creating Wenzel and Cassie states, on a multiplicity of scales, when the textured surface comes in contact with a hydrophobic/hydrophilic contact mixture. It is known in the art that the transition to the Wenzel state can be discouraged by the use of sharp cornered features in the plane of the surface. However, the occurrence of sharp cornered structures in natural structures, such as rose petals, is less common. Natural structures tend to possess rounded surface features, especially radiused or filleted corners. In nature, resistance to conversion to a Wenzel state seems to involve the creation of involute rounded structures rather than sharp edges. By involute it is meant concavity oriented in a line not orthogonal to the substrate surface. Such structures are difficult to create by an etching or casting method, but can readily be created by an embossing method that entails folding of a structure. Similarly, the Wenzel state can be discouraged by the use of curving communications between structures as opposed to straight line communication. In most cases, higher hydrophobicity equates with lower propensity for a Wenzel transition.

The hydrophobicity of a surface is enhanced by the placement of exterior corners around depressions. In some embodiments, this is achieved by the creation of additional pairs of adjacent depression walls that project into and are joined at the interior of the depression. In some embodiments this is achieved by designing an ordered array of depressions of a first hierarchy (examples: triangular, rectangular, pentagonal, or hexagonal shapes, regular or irregular; and further polygonal shapes defined generally by straight line segments). A second feature of smaller size and different hierarchical order is then superimposed on the depression wall of the first pattern. The method employed in creating such a structure may involve first emboss a large scale structure and then secondarily emboss additional smaller scale structure, preferably smaller scale structure embossed on larger scale structures.

Figure 3:
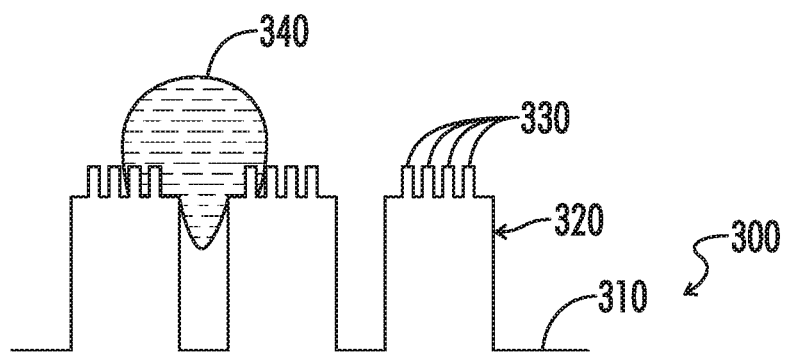
FIG. 3 depicts an embodiment of a microstructured surface useful for a glove.
Figure 4A:
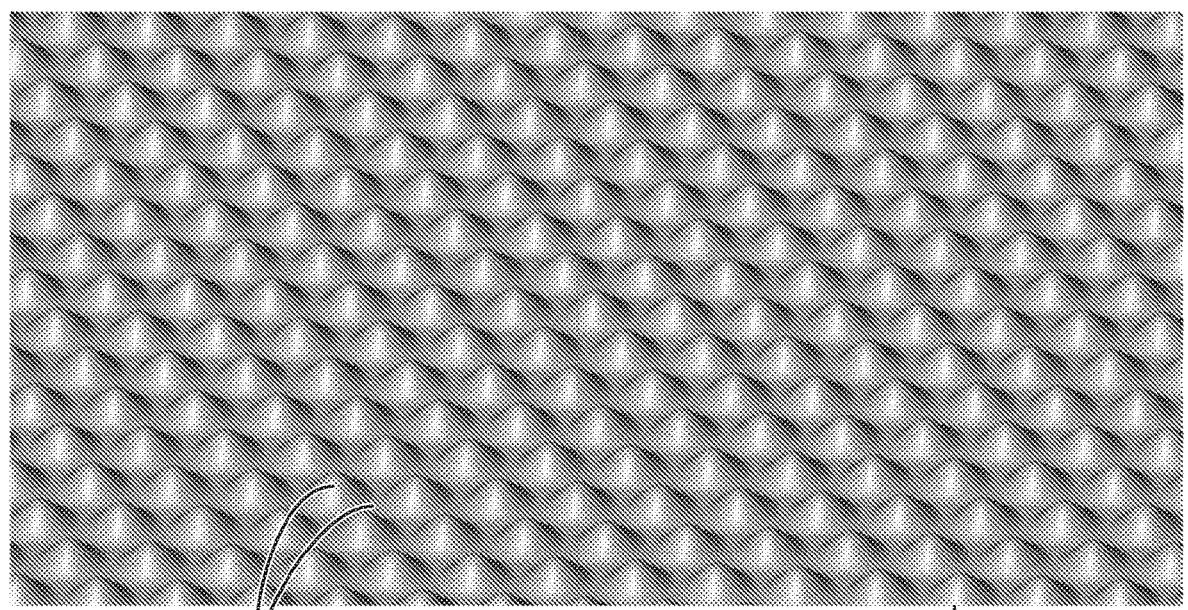
FIGS. 4A-4D depict a selection of substrates 410 having various sinusoidal waveform patterns that provide alternative curved surface texture features across substrate 410.
Figure 4B:
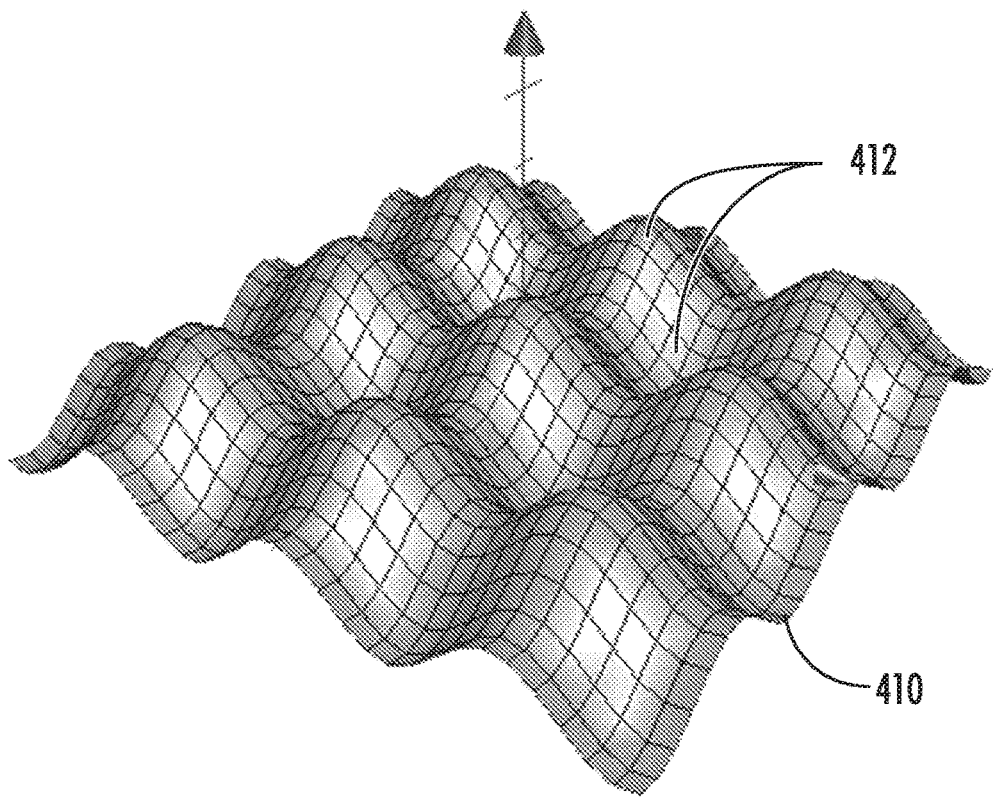
Figure 4C:
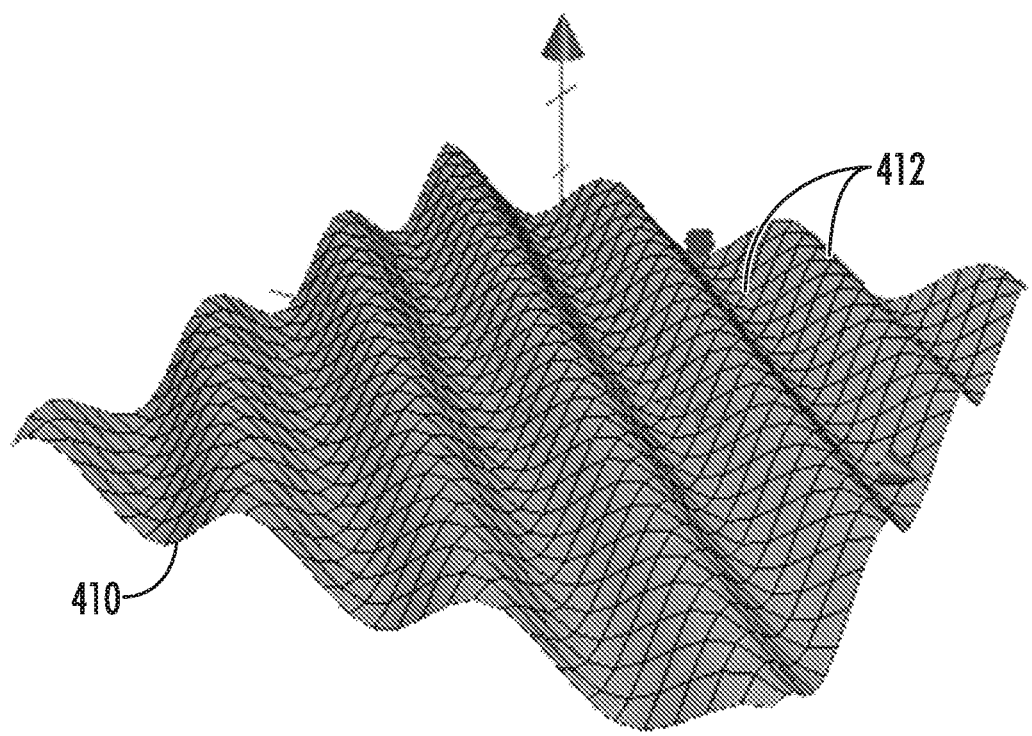
Figure 4D:
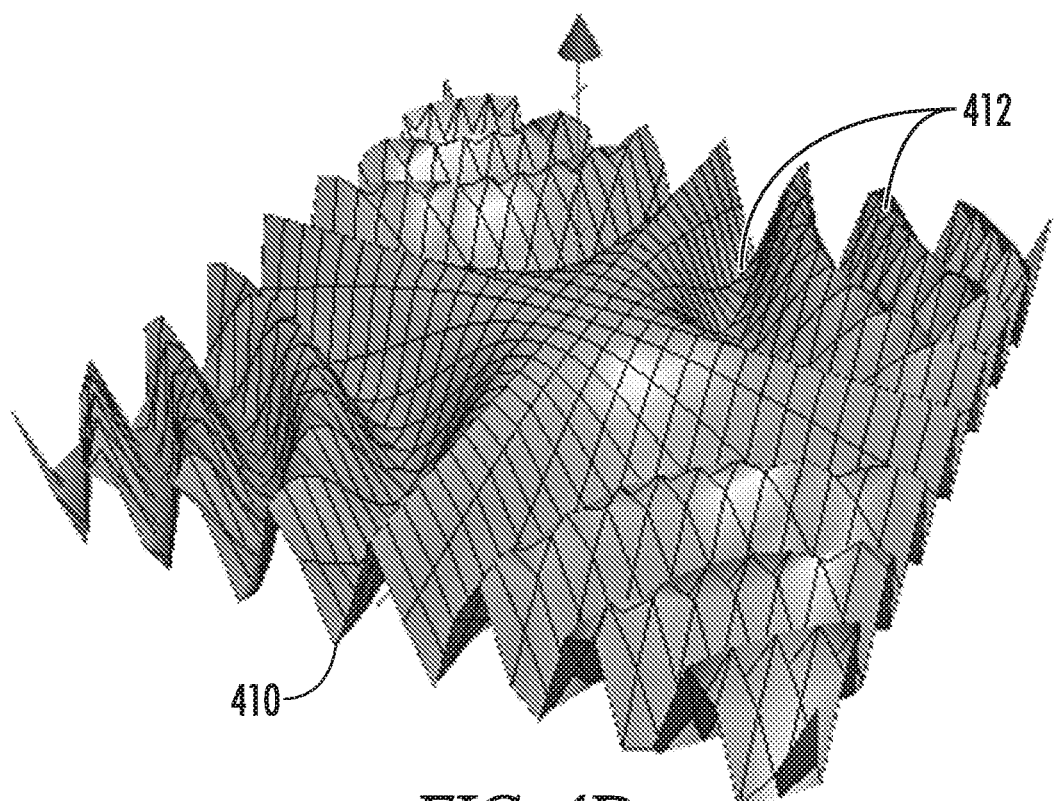

FIG. 3 depicts an embodiment of the surface texture 200, in which a Wenzel-Cassie state is formed with an aqueous liquid 240. The surface texture is provided on a substrate 210 and comprises a first microfeature of pillars 220 having a second set of pillars 230 disposed thereon.

According the present invention, the term sinusoidal waveform as used herein refers to a surface having a repetitive oscillation of rounded, nonflat curvature described by mathematical formulas incorporating trigonometric functions sine, cosine, tangent or exponential and power series functions. These mathematical formulas are used in computer aided design and computer aided manufacturing software to create texture surfaces using rapid prototyping, milling, electrical discharge machining or similar techniques to create a polymer or metal surface with the sinusoidal waveform texture features. The advantage of using mathematical formulas is that large numbers of rounded, nonflat features can be created rapidly in computer aided design and computer aided manufacturing software. Texture features of this type cannot be created using lithographic techniques.

Referring to FIGS. 4A-4D, a selection of substrates 410 are shown having various sinusoidal waveform patterns that provide alternative curved surface texture features across substrate 410. These embodiments are for illustrative purposes only as example embodiments of substrate 410 and are not limiting of the present invention and the term sinusoidal waveform as used herein.

According to the present invention, first set of texture features 412 includes dimensions selected from a size within a range of about 100 microns to about 1000 microns. More specifically as will be detailed herein below, in a preferred embodiment, the sinusoidal waveform is arranged so that first set of texture features 12 has sinusoidal rounded cavities of 750 microns, a pitch of 750 microns, and a depth of about 240 to 500 microns. This arrangement of the substrate is intended to promote an adhesive Wenzel-Cassie state with a hydrophobic/hydrophilic contact mixture.

Referring to FIGS. 5-8, a second set of texture features 514 is disposed on the surface of substrate 510. In one embodiment, second set of texture features 514 is molded on first set of texture features 512 of substrate 510. As detailed herein below, in one embodiment, substrate 510 is a compression molded polymeric material in which first and second sets of texture features 512, 514 are formed on substrate 510 during a single molding step. First and second sets of texture features 512, 514 cooperate to increase the surface area and affect at least one of adhesion, friction, hydrophilicity and hydrophobicity of substrate 510.

Preferably, the compression molded polymeric material forming substrate 510 is a environmentally durable polymer. In one embodiment, substrate 510 comprises polyethylene-nylon copolymer. In the illustrated embodiments, second set of texture features 514 is selected from the group consisting of microstructured projections and microstructured cavities, and combinations thereof. The illustrated embodiment in FIG. 3, second set of texture features 314 comprise microstructured cavities extending downwardly into substrate 310.

Further in FIGS. 5-8, a second set of texture features 514, 614, 714 and 814 comprise microstructured projections extending upwardly from substrate 510, 610, 710 and 810, respectively. Preferably, in the illustrated embodiments of FIGS. 5-8, the microstructured projections of said second set of texture features 514, 614, 714, 814 comprise generally cylindrical pillars.

Figure 5:
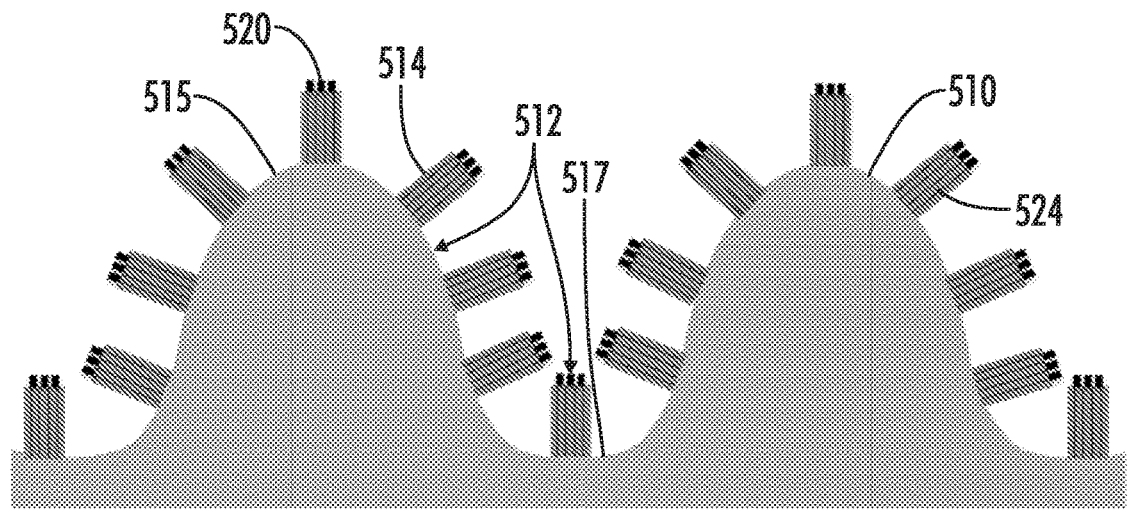
FIG. 5 depicts a cross sectional view of an embodiment of the microstructured surface on a substrate according to the present disclosure.
Figure 6:
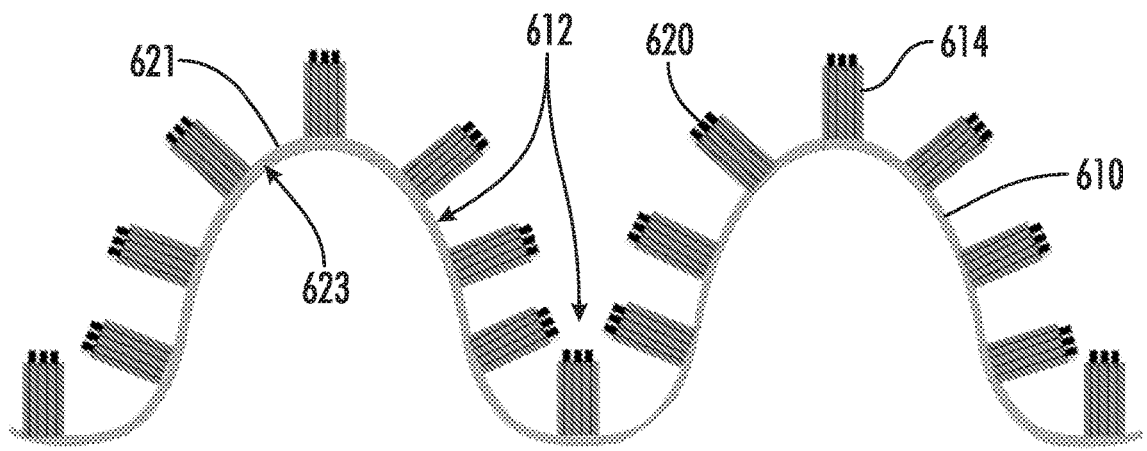
FIG. 6 depicts a cross sectional view of a microstructured surface on a thin film substrate according to the present disclosure.

Preferably, in the illustrated embodiment of FIG. 3, the microstructured cavities of second set of texture features 314 comprise generally cylindrical recesses. Referring to FIG. 5, in one embodiment in which substrate 510 is a thin film substrate and has operable opposing top and bottom surfaces, first set of texture features 512 disposed on a top surface 521 of substrate 510 form a complementary shape on a bottom surface 523 of substrate 510 so that a rounded peak on top surface 521 forms a rounded valley on bottom surface 523 and the rounded valley on top surface 521 forms a rounded peak on bottom surface 523.

Referring again to FIG. 5, in an embodiment in which substrate 510 is a thin film substrate and has operable opposing top and bottom surfaces, second set of texture features 514 includes a series of microstructured projections on one of top surface 521 and bottom surface 523 of substrate 510, which then define a series of complementary microstructured cavities on the other of said top surface and said bottom surface 521, 523. Likewise, in an embodiment in which second set of texture features 514 comprises microstructured cavities which project downwardly through substrate 510 from a top surface 521, they form complementary microstructured projections on the opposing bottom.

Referring to FIGS. 2 and 5, in the illustrated embodiments, second set of texture features 214, 514 include at least a portion of texture features that extend along an axis normal to the curve of the sinusoidal waveform of substrate 210 and 510, respectively, at a given point for the individual microstructure. In this way, second set of texture features 214, 514 follow the curvature of first set of texture features 212, 512.

According to the present invention, second set of texture features 514 includes dimensions selected from a size within a range of about 10 microns to about 100 microns. Further, second set of texture features 514 preferably have a height to width aspect ratio of less than 5, and a minimum spacing of 1 micron between each texture feature of said second set of texture features to maintain structural strength while allowing for liquid flow and penetration between the individual microstructures comprising second set of texture features 214.

Referring again to FIGS. 5-8, a third set of texture features 520, 620, 720, 820 may also be disposed on substrate 510, 610, 710, 810, respectively. Preferably, third set of texture features 520, 6120, 720, 820 is selected from the group consisting of microstructured projections and microstructured cavities, and combinations thereof. In one embodiment, the microstructured projections of third set of texture features comprise generally cylindrical pillars.

Referring again to FIG. 3, in one embodiment, the microstructured cavities of third set of texture features 320 comprise generally cylindrical recesses. Preferably, third set of texture features 320 are compression molded simultaneously with first and second sets of texture features 312, 314. In a further preferred embodiment, third set of texture features 320 have a height to width aspect ratio of less than 5, and a minimum spacing of 1 micron between each texture feature of third set of texture features 320 to maintain structural strength while allowing for liquid flow and penetration between said third set of texture features. The aspect ratio is smaller when devices are made of lower strength materials and larger when made from stronger materials. The spacing between features is smaller for less viscous liquids and larger for more viscous.

Referring to FIGS. 2 and 5, in the illustrated embodiments, third set of texture features 220 and 520 include at least a portion of texture features that extend along an axis normal to the curve of the sinusoidal waveform of substrate 210 and 510, respectively. For purposes of the present invention in which the second and third sets of texture features 214, 514, 220, 520 extend along an axis normal to the curve of the sinusoidal waveform, the normal line to a curve is the line that is perpendicular to the tangent of the curve at a particular point. In the illustrated embodiments, second set of texture features 214, 514 is smaller than first set of texture features 212, 512 and third set of texture features 220, 520 is smaller than second set of texture features 214, 514.

According to the present invention, third set of texture features 220 includes dimensions selected from a size within a range of about 1 micron to about 10. Referring to FIGS. 5-8, in one embodiment, the third set of texture features are disposed on an end surface 522, 622, 722, 822 of second set of texture features 14.

In a further advantageous embodiment, third set of texture features 520, 620, 720, 820 are disposed on first set of texture features 512, 612, 712, 812 between second set of texture features 514, 614, 712, 814. In a further advantageous embodiment, third set of texture features 520, 620, 720, 820 are disposed on an end surface 522, 622, 722, 822 of second set of texture features 514, 614, 712, 814. as well as, disposed on first set of texture features 512, 612, 712, 812 between second set of texture features.

Figure 7:
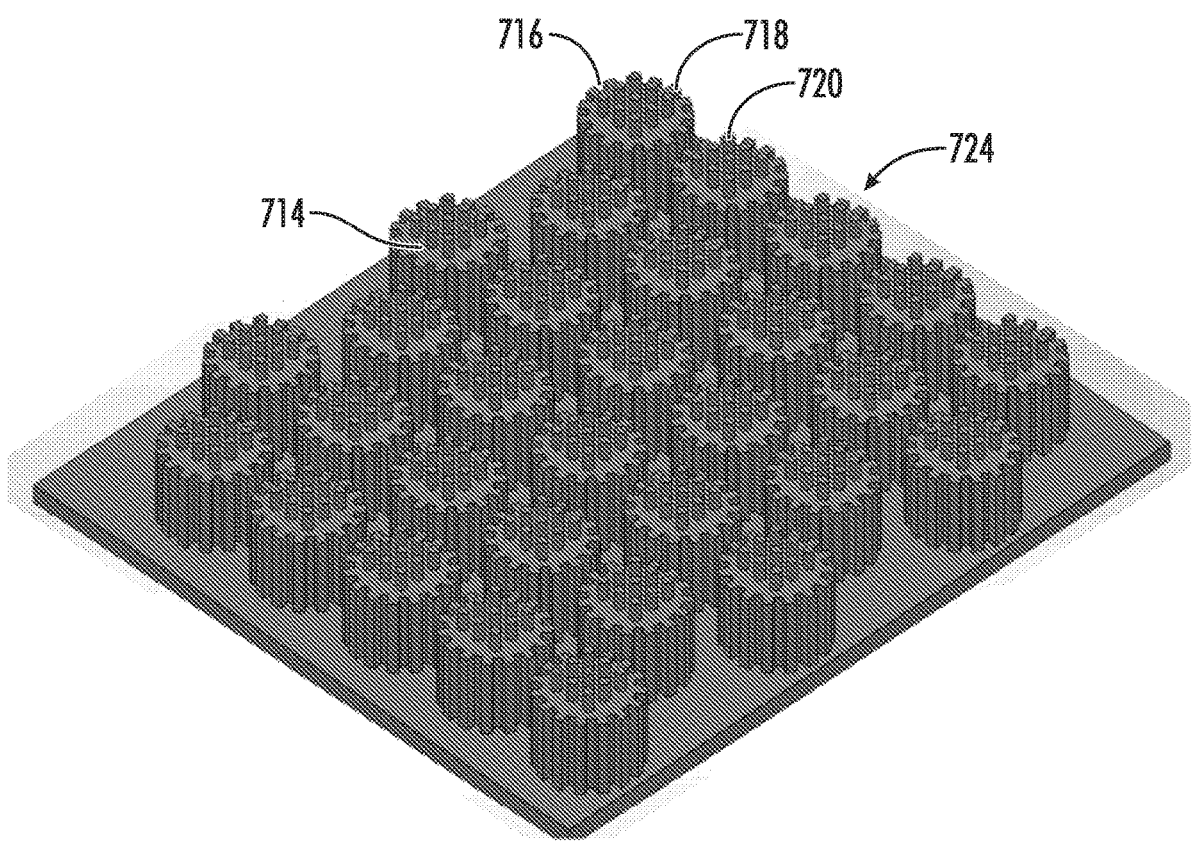
FIG. 7 depicts a perspective view of a microstructured surface having a four sets of microfeatures.
Figure 8:
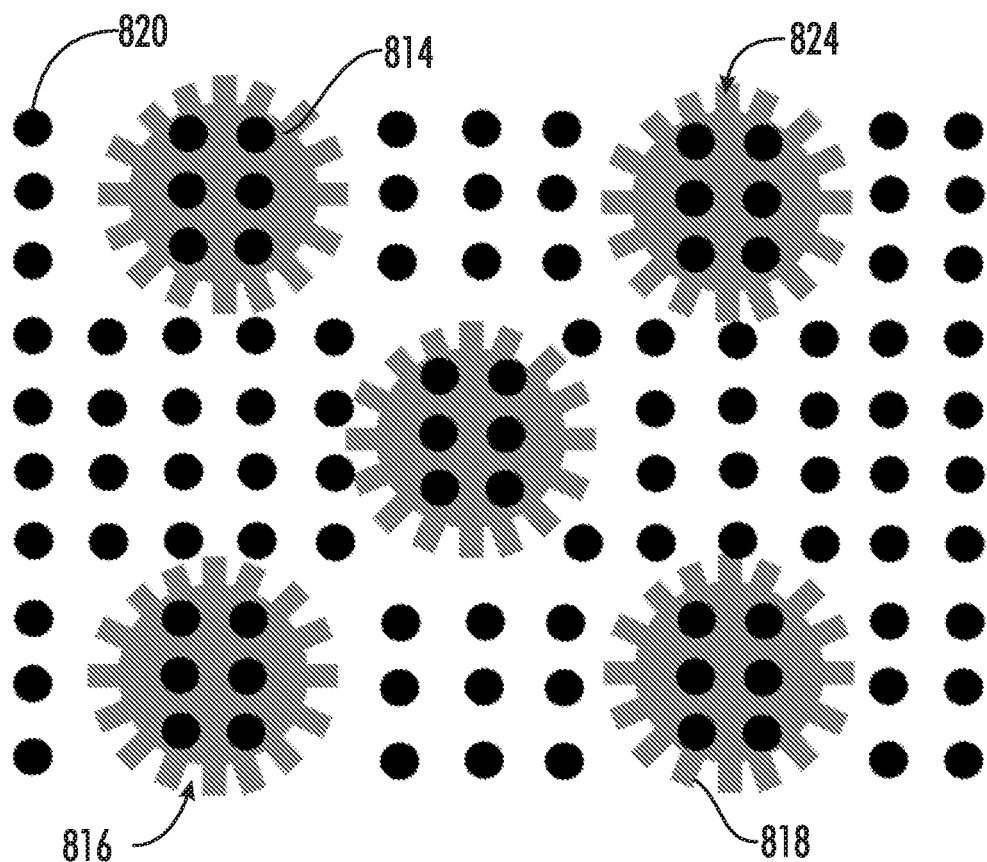
FIG. 8 depicts a schematic top view of a microstructured surface having four sets of microfeatures.

Referring to FIG. 7, a fourth set of texture features 724 may be disposed on side surfaces of second set of texture features 714. Fourth set of texture features 724 is selected from the group consisting of flutes 716 and ribs 718, and combinations thereof. In the illustrated embodiments, flutes and ribs 716, 718 run vertically along the height of the side surfaces on the outside circumference of each microstructure comprising said second set of texture features 714. Fourth set of texture features 724 preferably include dimensions selected from a size within a range of about 1 micron to about 10 microns. Preferably, fourth set of texture features 724 are compression molded simultaneously with said first, second, and third sets of texture features into substrate 710.

Preferably, flutes and/or ribs 716, 718 with features and spacing larger than 1 micron are added to the exterior of the cylindrical pillars or cavities defining second set of texture features 714 to both add surface area and to increase structural resistance to bending and breaking. The spacing between individual microstructures of fourth set of features 714 is smaller for less viscous liquids and larger for more viscous liquids. Third set of texture features 720 cover both the tops of pillars and bottoms of cavities and the area between the pillars or cavities defining second set of texture features 714 in a substantially uniform manner. Together the second and third sets of texture features 714, 720 substantially increase the surface area exposed to the liquid covering the opposite surface from substrate 710.

Depending on the desired application, the first, second, third and fourth sets of texture features cooperate to increase the surface area of substrate 710 to effect at least one of adhesion, friction, hydrophilicity and hydrophobicity of substrate 710. In one embodiment, the substrate has a surface adhesion with a sliding friction force of greater than 50 gr/cm2 when applied against a surface comprising a hydrophobic/hydrophilic mixture.

In a preferred embodiment, the substrate has a surface adhesion with a sliding friction force of about 325 gr/cm2 when applied against a surface comprising a hydrophobic/hydrophilic mixture. In early studies, the inventors characterized rose petal structures and observed a 'rolling hill' effect in microstructures. Additionally, smaller microstructures were noted as 'hairs' that seemed to contribute strongly to the superhydrophobic effect. In order to best simulate this scheme, the inventors created sinusoidal designs as set forth herein that could reproduce and improve upon rounded microstructure effects seen naturally, starting with a sinusoidal waveform substrate with features from 300 microns diameter and pitch of 100 microns. The dimensions for the third set of texture features include in one embodiment pillars having 3 micrometers diameter, 6 micrometers pitch, and 5 micrometers tall. The second set of texture features in one embodiment includes fluted microstructure pillars that are at least 35 micrometers in diameter, 35 micrometers tall, and 10 micrometers spacing. When overlapped together, the second and third sets of micro features are formed along an axis normal to the surface of the sinusoidal waveform features (see, e.g., FIGS. 5 and 6). These are also maintained multidimensionally over the round To improve the superhydrophobic effect found in nature with the rose petal, second set of texture features, e.g., 714 was added with 'fluted' or 'ribbed' features running down the side surface. These fluted and ribbed features that define fourth set of texture features 724 simulate the smaller, hair like microstructures of the rose petal to further promote hydrophobocity. Accordingly, each microstructure of said first, second, third and fourth sets of texture features 712, 714, 720 and 724 have a respective pitch, height/depth, and diameter, and wherein are arranged so that liquids penetrate between at least said first and second sets of texture features in a Wenzel fully wetted state when applied against a liquid covered surface to promote adhesion between substrate 710 and the adjacent surface.

Preferably, the sinusoidal waveform of first set of texture features 712 includes rounded peaks that facilitate pressure distribution across substrate 710 when pressed against a liquid covered surface. Preferably, second and third sets of texture features 714, 720 are uniformly distributed across the rounded peaks of first set of texture features 712 provide increased surface area to first set of texture features 712. The rounded peaks define areas of increased pressure when substrate 710 is applied against a liquid covered surface that promote a transition of liquid droplets from a suspended Cassie-Baxter state to a Wenzel fully wetted state among at least said first and second sets of texture features. In a preferred embodiment, first, second and third sets, e.g., 712, 714, 720 of texture features allow for liquid penetration to a Wenzel fully wetted state, while the fourth set of texture features 724 are constructed and arranged to maintain superhydrophobic characteristics. The function of the second and third sets of texture features 714, 720 is to create a large surfaces area simultaneously with spacing wide enough the viscous liquids can flow through the structure at low pressure. Low pressure in this application is defined in the context of the weight associated with liquid droplets being sufficiently to create a Wenzel fully wetted state to promote adhesion of substrate 710 to an adjacent liquid covered surface. Accordingly, the microstructured surfaces of the present invention are designed to facilitate transitions from a Cassie-Baxter suspended droplet state to the Wenzel fully wetted state with a water droplet of greater than 10 texture liters in size.

One function of the sinusoidal waveform of first set of texture features 12 is to further increase the surface area while creating areas of increased pressure at the peaks of the features. These areas of increased surface area wet first, causing a rapid transition from the Cassie-Baxter suspended droplet state to the Wenzel fully wetted state. A second function of the sinusoidal waveform of first set of texture features, e.g., 612 is to keep the peak pressure low enough and to spread the pressure such that there is little or no penetration through the liquid layer on the surface into the underlying material. The second and third sets of texture features 614, are spread uniformly over the sinusoidal waveform of first set of texture features 612 and are normal to the curve of the surface. That is they are perpendicular to a surface tangent at each point of the microstructure on surface. This ensures that the maximum surface area is created in a structure that can be molded.

Figure 9:
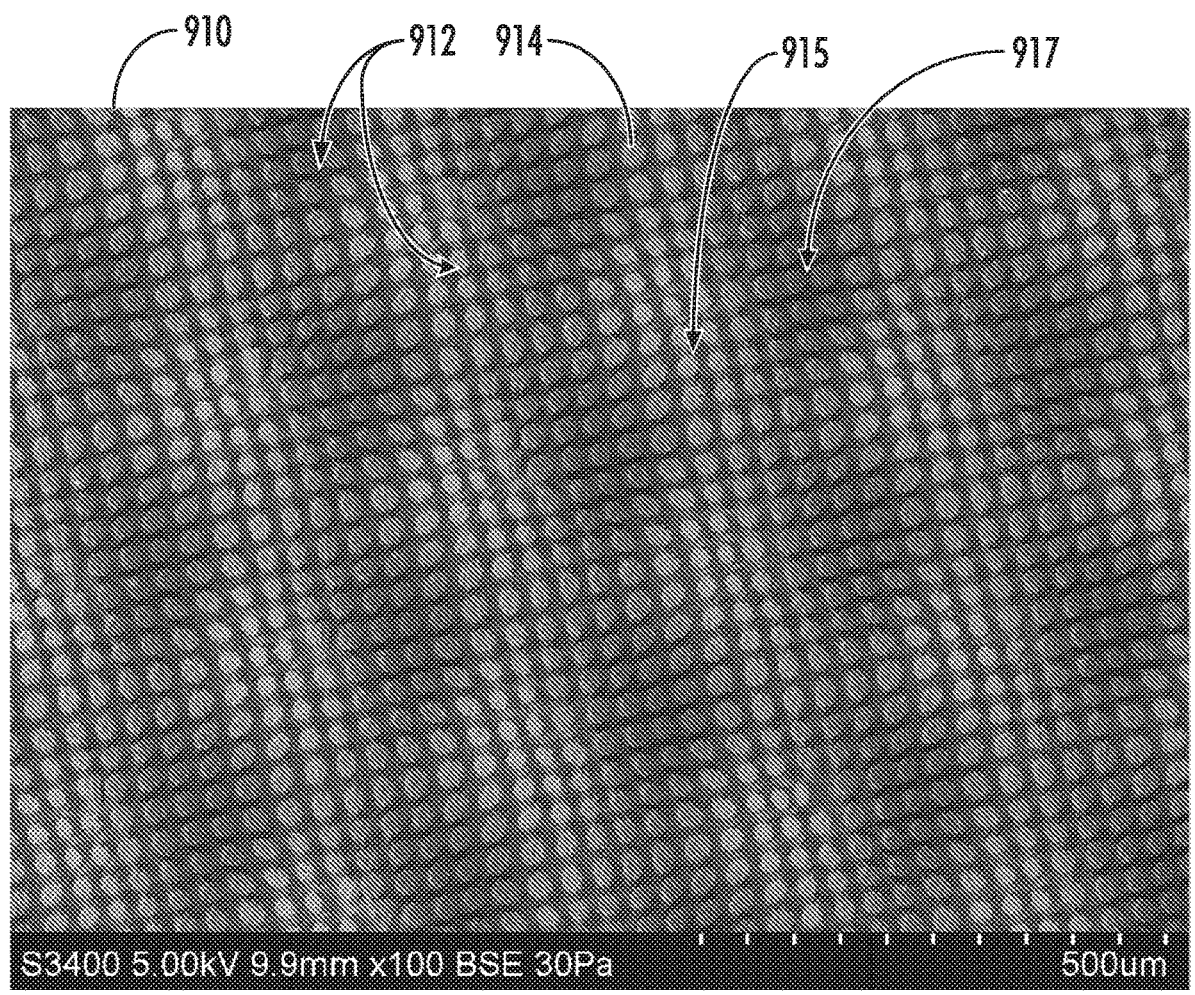
FIG. 9 is an image of an embodiment of surface useful for adhesive glove.

Referring to FIG. 9, a first embodiment of a textural arrangement on a textured surface according to the present invention is shown comprising a substrate, designated generally as 910. In the illustrated embodiment, substrate 910 has a sinusoidal waveform comprising a series of rounded peaks and valleys that produce a continuously curving surface across at least a portion of substrate 910. The sinusoidal waveform of substrate 910 defines a first set of large scale features, designated generally as 912. In FIG. 2, substrate 910 is constructed and arranged to focus on a series of rounded knobs forming peaks 915 projected upwardly from the surface with associated valleys 917 disposed between peaks 915.

Figure 10:
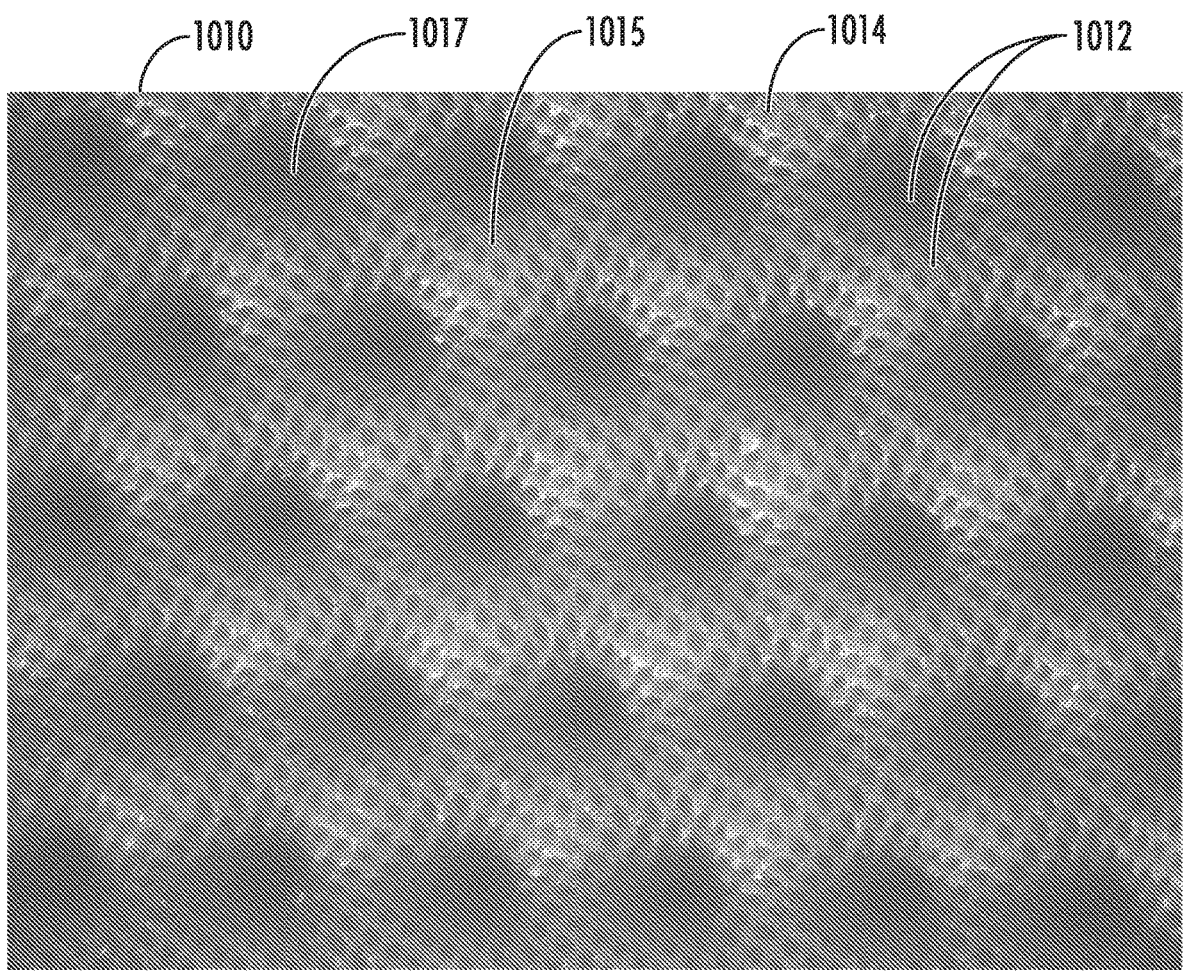
FIG. 10 is an image of an embodiment of microstructured surface having an inverse (concave) pattern.
Figure 11A:
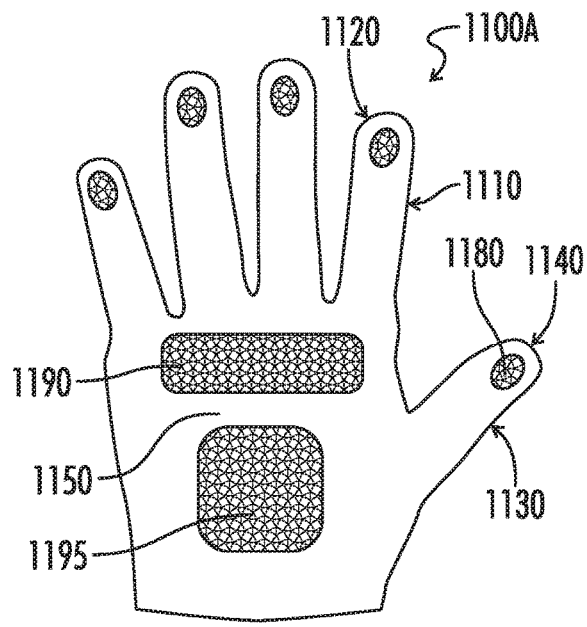
FIGS. 11A-D depict several embodiments of gloves comprising a hierarchical surface texture.
Figure 11B:
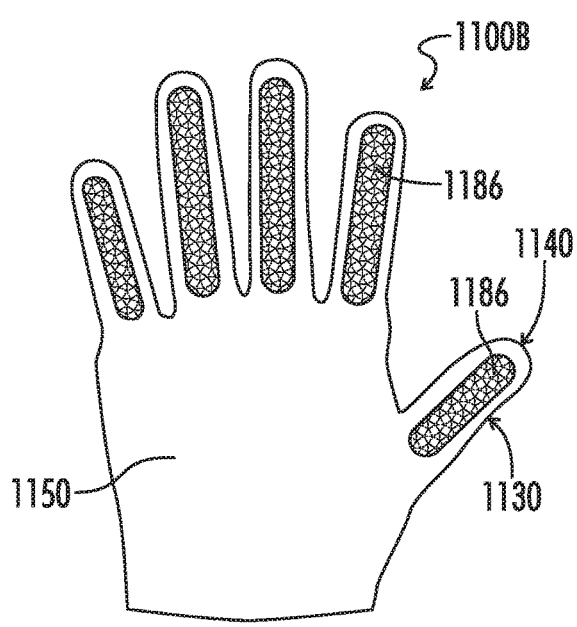
Figure 11C:
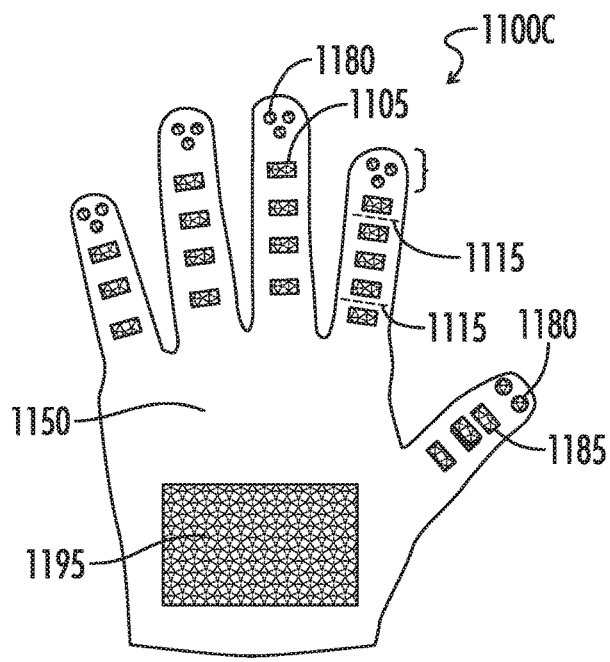
Figure 11D:
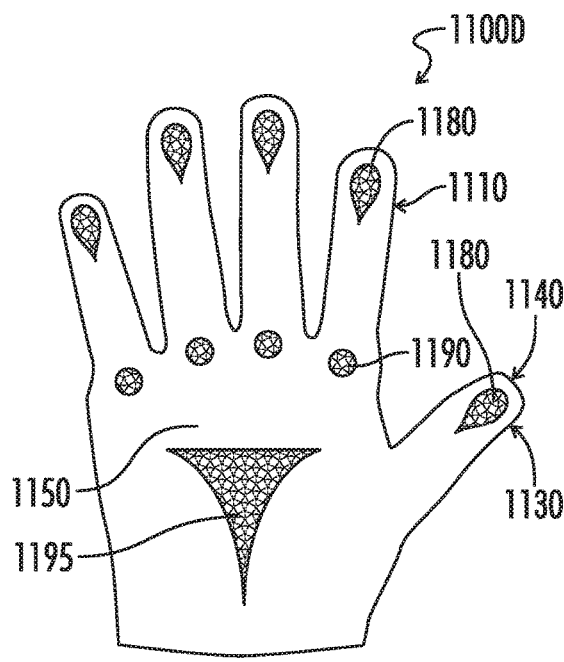

In a second embodiment shown in FIG. 10, the inverse arrangement is shown in which substrate 1010 is constructed and arranged to focus on a series of rounded cavities forming valleys 1017 extending inwardly into substrate 1010 as the dominant feature with the associated peaks 1015 disposed between valleys 1017. In both embodiment, the surface of substrate 1010 is continuously curving throughout sinusoidal waveform pattern area.

FIGS. 11A-11D depict alternative embodiments of glove comprising a hierarchical surface pattern disposed in various arrangements on the fingers, thumbs and palms. The patterns may be disposed on both the front and back of the glove to produce an ambidextrous glove. The textured surfaces 1180 can be placed at positions useful to grasping and manipulating surgical devices and slippery tissue. The geometry of the island structures can be selected to be consistent with normal bending action and typical points of contact. For example, in the finger tip area can be circular, square, rectangular, or tear shaped. In regions where the fingers bend the islands are linear 911 and arranged parallel 913 to the line of finger bending 915. In the palm area where articulation is absent, a larger island 917 substantially covering the entire surface of the palm may be selected.

The pattern as generally depicted in FIG. 2 can be formed on a glove by a dipping process. It should be understood to one of ordinary skill in the art that a glove former may be used to manufacture a glove with the texture as described in various embodiments herein. Gloves made by a form dipping process are of a unitary construction (i.e. without seems). The form is patterned with the inverse or negative of the desired pattern, such that when the form is coated with a suitable elastomeric polymer, and the polymer is cured, the inner surface in contact with the form acquired the negative of the pattern on the form.

The glove may be constructed by first dipping the glove former into a quantity of liquid containing natural or synthetic rubbers such as acrylonitrile-butadiene (nitrile), polychloroprene, polyvinyl chloride latex, or any suitable material or combinations of the like. Next, the coated former is removed from the liquid material allowing the liquid coating to solidify to the former surface where the now solid state material can then be removed as a uniform glove.

It should be readily understood that the glove former used herein preferably comprises a series of hierarchically superimposed features as described in FIG. 1. The features can be pillars, pillars with fins along their axial length, undulating mounds of approximate two-dimensional sinusoidal profile, pyramids, or any concave shape. The glove is removed from the form by inversion. Inversion is a procedure by which the surface of the glove in contact with the form is inverted so that it becomes the outer surface of the glove. The outer surface of the glove is consequently textured with convex shapes.

Pattern may be applied to the palm side of the glove and also the backhand side of the glove. Patterning in this way makes the glove ambidextrous. Due to the ambidextrous nature of the glove, the glove may be placed on either hand allowing both the first side and a second side to be arbitrarily referred to as either the palm side or back of the hand side depending on which hand the glove is placed on.

With respect to the two sided nature of the glove, a glove may comprise: a first palm region and a second palm region which are adapted to cover the palm and back of a person's hand; a first thumb region and a second thumb region adapted to cover the thumb of a person's hand and extending outwardly from the first and second palm region; a first index finger region and a second index finger region adapted to cover the index finger of a person's hand and extending outwardly from the first and second palm region; a first middle finger region and a second middle finger region adapted to cover the middle finger of a person's hand and extending outwardly from the first and second palm region; a first ring finger region and a second ring finger region adapted to cover the ring finger of a person's hand and extending outwardly from the first and second palm region; a first little finger region and a second little finger region adapted to cover the little finger of a person's hand and extending outwardly from the first and second palm region; a first wrist region and a second wrist region adapted to cover a person's wrist and extending outwardly from the first and second palm region; and a first cuff region and a second cuff region adapted to cover a portion of a person's arm and extending outwardly from the first and second wrist regions, with the respective first regions located on the first side and the second regions located on the second side of a glove.

In preferred embodiments, the glove may comprise a continuous, textured surface that may cover portions of the palm region, thumb region, index finger region, middle finger region, ring finger region, and little finger region. In further preferred embodiments, the glove may comprise a first continuous textured surface on the first side that may cover portions of the first palm region, first thumb region, first index finger region, first middle finger region, first ring finger region, and first little finger region. Also in further preferred embodiments, the glove may comprise a second continuous textured surface on the second side that may cover portions of the second palm region, second thumb region, second index finger region, second middle finger region, second ring finger region, and second little finger region.

In other preferred embodiments, the glove may comprise a first continuous textured surface on the first side that may cover portions of the first palm region, first thumb region, first index finger region, first middle finger region, first ring finger region, first little finger region, and/or first wrist region. Also in other preferred embodiments, the glove may comprise a second continuous textured surface on the second side that may cover portions of the second palm region, second thumb region, second index finger region, second middle finger region, second ring finger region, second little finger region, and/or second wrist region.

In still further preferred embodiments, the glove may comprise one or more first small hierarchical textured surfaces on the first side and/or one or more second small hierarchical textured surfaces on the second side. In some embodiments, one or more first small hierarchical textured surface may be located on the first wrist region and/or the first cuff region of the first side. In other embodiments, one or more second small hierarchical textured surface may be located on the second wrist region and/or the second cuff region of the second side.

Also, a glove may comprise what is known in the art as a necklace with a generally smooth necklace surface free from texturing that is preferably continuous with the glove surface and that may extend from the bead of the little finger region side of the glove up, around, and down the side of the palm region, wrist region, cuff region, each finger region, the side of the thumb region, and ending at the bead of the thumb region side of the glove. In some embodiments, a necklace surface of a necklace may form a boundary between or otherwise separate a first continuous textured surface on a first side from a second continuous textured surface on a second side of the glove.

A necklace may not directly be involved in gripping an object, yet it influences the grip by virtue of its greater elastic and flexible allowances than the allowances of the continuous textured surface to ensure the glove has maximum resilience for all gripping requirements. In preferred embodiments, the glove comprises a necklace which further comprises a generally smooth necklace surface of an optimum width running across the longitudinal periphery of all the finger regions and thumb region. The smooth necklace surface of the necklace compensates for any stiffness rendered or impaired by the continuous and small hierarchical textured surfaces on the actual working surface of the glove. A smooth necklace surface that runs across the finger and thumb regions of the glove comprises an optimum width to ensure that the necklace generally does not interfere or come in contact with the gripping object and also at the same time enables excellent flexing and thus preventing fatigue.

Common user practices show a tendency of using double currently available gloves by using a currently available liner or supplementary glove inside a currently available main glove for sweat management and to prevent slip inside the glove due to moisture as the currently available gloves comprise a mostly loose fit.

These currently available gloves consist of a loose palm but narrow finger circumference which often results in occupational fatigue to the user while donning the main currently available glove over the currently available supplementary glove. Currently available gloves are difficult to place on the hand with a secondary liner glove inside. The narrow fingers circumference with a liner glove inside was making the gloves a tight fit and that in turn causes occupational discomfort while two currently available gloves were on. Also the tight fit of the currently available gloves restricts the bending ease of the fingers and eventually the user will complain of stiffening feeling in the fingers and palm.

In a particular embodiment of the present invention, texture is applied on the interior surface as well as the exterior surface. The interior texture provides adherence between the hand and the glove, as well as a channel structure between glove and hand. The Cassie component of the hierarchical Wenzel-Cassie surface wicks moisture away from the hand. This is the same principle which contributes to the adhesive nature of the exterior surface of the glove when placed in contact with tissue. Part of this adhesive functionality is characterized by removal of the continuous exudation of aqueous media from tissue surfaces.

Accordingly, in the manufacture of a interior/exterior textured glove the usual dipping form needs to be mated with and enclosing form. Such an enclosing form would be two part, like a clam shell. On the interior of this enclosing form is disposed the textured surface. And on the surface of the dipping form is disposed another texture. Preferably, both textures are of the type disclosed herein.

Manufacture comprises the steps of 1) dipping the dipping form in a suitable polymeric solution, 2) allowing the polymeric solution coating the dipping form to shed the excess, 3) while the polymeric solution is still moldable the enclosing form is closed around the dipping form so as to encapsulate it, 4) the arrangement of dipping form and enclosing form is held until the polymeric solution hardens, and 5) the enclosing form is opened and the glove is peeled from the dipping form.

The enclosing form may be gas permeable to allow solvent in the polymeric solution to be lost. Optionally, the enclosing form or dipping form may be heated. Alternatively, other casting methods are known in the art. For example, reaction-in-mold injection molding, or melt injection molding.

The former may be the mirrored inverse structure of the enclosing form with respect to a large scale feature of the pattern. For example, on the form side, the largest scale structure may be a two-dimensional sinusoid and and the enclosing form side the largest scale structure may be a two-dimensional sinusoid of same amplitude and spatial frequency by shifted 180 degrees in both directions, such that the raised portions of the form coincide spatially with the depressed portions of the enclosing form. The result is an undulating surface upon which are deposed finer structure on both the form side and the enclosing form side.

The enclosing form textures an outer side and the enclosing form textures an inner side, so that the glove is reversible with the first side and second side forming generally mirror images of each other with respect to the largest scale structure.

Patterns have been tested in shear using an Instron force tester, in which the force required to displace a pattern along a plane was measured. The test results illustrate the particular advantage of a hierarchical structure. The hierarchical structure is comprising first layer L1 comprising small pillars (6 microns pillar pitch, 5 microns tall) disposed on the flat surface of second layer L2 comprising large pillars (25 microns pillar pitch, 30 microns tall) with 3 micron flute width, 6 micron flute pitch, 5 micron flute depth, and second layer is disposed on third layer L3 comprising a continuous two-dimensional sinusoidal surface. The test articles are:

86A Combination of L1 and L2
87A—1.3: 450 micron sinusoids, 450 micron pitch, 300 micron depth
88A—L3: 600 micron sinusoids, 600 micron pitch, 400 micron depth
89A—L3: 750 micron sinusoids, 750 micron pitch, 500 micron depth
90A—Combination of pattern 086A and 087A (L3 90 micron sinusoid depth)
91A—Combination of pattern 085A and 088A (L3 160 micron sinusoid depth)
92A—Combination of pattern 085A and 089A (L3 205 micron sinusoid depth)

The enclosing form textures an outer side and the enclosing form textures an inner side, so that the glove is reversible with the first side and second side forming generally mirror images of each other with respect to the largest scale structure. The casting polymers polylactic acid polymer (PLA) and polyurethane (AP) dissolved in acetone.

Mechanical localization characteristics were assessed. Cutlets of bovine "steak" were purchased and sliced into 3 cm cubes and affixed to a localized platform. The meat was kept well hydrated with physiologic saline solution at 22° C. Test articles were cut to 1×1 cm squares and mounted on discs to which was attached the filament through which force would be applied to the test article. Shear was measured by placing the strip on the 3 cm cube of meat and pulling horizontally to the surface. Thus these measurements yield a force per unit area.

In these tests we used moist meat rather than water-immersed to better reflect surgical conditions. In all measurements, clear outliers were discarded, and the run was repeated with additional test articles. An Instron Mini 55 was used to record force and the crosshead speed was 0.1 cm/sec. The load cell limit was 200 g with an accuracy of +/−0.1 g.

| Texture | Moist meat (grams force) | |
|---|---|---|
| 093A, (PLA) | N = 10 | 148 +/− 20 |
| 093A, (AP1780) | N = 10 | 84 +/− 12 |
| 093A, (AP1959) | N = 10 | 89 +/− 19 |
| 094A, (PLA) | N = 10 | 169 +/− 28 |
| 094A, (AP1780) | N = 10 | 92 +/− 7 |
| 094A, (AP1959) | N = 10 | 95 +/− 14 |
| 095A, (PLA) | N = 10 | 174 +/− 22 |
| 095A, (AP1780) | N = 10 | 112 +/− 23 |
| 095A, (AP1959) | N = 10 | 117 +/− 12 |
| 093A, (PLA) | N = 10 | 168 +/− 33 |
| 094A, (PLA) | N = 10 | 177 +/− 28 |
| 095A, (PLA) | N = 10 | 185 +/− 19 |
| 086A, (PLA) | N = 10 | 76 +/− 12 |
| 074A, (PLA) | N = 10 | 118 +/− 12 |
| 090A, (PLA) | N = 10 | 88 +/− 20 |
| 091A, (PLA) | N = 10 | 91 +/− 15 |
| 092A, (PLA) | N = 10 | 102 +/− 16 |
| 074A, (PLA) | N = 10 | 127 +/− 18 |
| Smooth (PLA) | N = 10 | 5 +/− 5 |

The arrangement of hierarchical structures may be geometric and describable generally with a mathematical equation. Alternatively, the hierarchical structures may be randomly disposed, possibly with varying pitch, which is more typical of natural structures. The arrangement of hierarchical structure can generally be described by a fractal dimension. A fractal dimension is a statistical quantity that gives an indication of how completely a collection of structures appears to fill space, in the present case a plane, as one examines that structure on a multiplicity of spatial scales Specifying a fractal dimension, which is statistical in nature, does not necessarily indicate that the hierarchical structure is well defined by a mathematical equation. Generally, a random arrangement of structures within a specific scale possesses a higher fractal dimension than one in which the structure is mathematically described at all points on a surface. Thus, a random structure may possess an advantage in the aspect that a adhesive surface of the present invention has greater utility when interacting with a natural surface. A higher fractal dimension within a specific spatial scale may be achieved by applying to a substrate multiple pitch arrangements. The protuberances and depressions may be locally scaled with respect to the local pitch. Accordingly, the pitch may vary within a scale structure. In the practical realization of higher fractal dimension structures, the variation of the pitch may be describable by a mathematical equation, for example, a sinusoidal variation of pitch, which would have utility in mimicking natural surfaces.

Generally, structures can be described as sharp-edged or rounded, and this feature is not typically captured by a fractal dimension. Another structural aspect not addressed by the above descriptive parameters is the degree of communication between structures. By communication, it is meant that a structure, such as a protuberance or a depression, has a spatial extent greater than the pitch. For example, a valley surrounding a protuberance may be connected to another valley surrounding another protuberance, thus the depressions are said to be communicating whereas the protuberances are not. The communication may range from 1 to about 1000, more particularly the communication may extend over the entire surface of the substrate.

These structures are constructed with the purpose of creating Wenzel and Cassie states, on a multiplicity of scales, when the adhesive textile of the present invention comes in contact with a hydrophobic/hydrophilic contact mixture. It is known in the art that the transition to the Wenzel state can be discouraged by the use of sharp cornered features in the plane of the surface. However, the occurrence of sharp cornered structures in natural structures, such as rose petals, is less common. Natural structures tend to possess rounded surface features, especially radiused or filleted corners. In nature, resistance to conversion to a Wenzel state seems to involve the creation of involute rounded structures rather than sharp edges. By involute it is meant concavity oriented in a line not orthogonal to the substrate surface. Such structures are difficult to create by an etching or casting method, but can readily be created by an embossing method that entails folding of a structure. Similarly, the Wenzel state can be discouraged by the use of curving communications between structures as opposed to straight line communication. In most cases, higher hydrophobicity equates with lower propensity for a Wenzel transition.

The hydrophobicity of a surface is enhanced by the placement of exterior corners around depressions. In some embodiments, this is achieved by the creation of additional pairs of adjacent depression walls that project into and are joined at the interior of the depression. In some embodiments this is achieved by designing an ordered array of depressions of a first hierarchy (examples: triangular, rectangular, pentagonal, or hexagonal shapes, regular or irregular; and further polygonal shapes defined generally by straight line segments). A second feature of smaller size and different hierarchical order is then superimposed on the depression wall of the first pattern. The method employed in creating such a structure may involve first emboss a large scale structure and then secondarily emboss additional smaller scale structure, preferably smaller scale structure embossed on larger scale structures.

The methods of manufacture of non-woven adhesive textiles of the present invention include lithography, casting, extrusion/embossing, and any of several methods for transferring a texture to a surface. A preferred method is embossing, where a polymeric substance is heated to a molten state and passed through dual rollers, at least one of which contains a negative image of the desired embossed structure. A small scale texture is embossed on a planar sheet. This embossed planar sheet is heated to a malleable but not fluid state and passed through dual rollers possessing a medium scale texture which impresses an inverse image. This process can be repeated multiple times. The medium scale texture is large relative to the small scale texture, thus the impression of the medium scale texture folds the small scale texture, making possible involute structures which would ordinarily not be possible with a lithography or casting method.

The adhesive textiles of the present invention have three or more levels of textures assembled in a manner to yield a high surface area while maintaining a minimum spacing between textures to allow for liquid flow and penetration to promote in the first instance surface washing and in the second instance surface adhesion; and while maintaining a minimum structural strength obtained by keeping height to width aspect ratio of all features below a critical level at which material strength is exceeded.

According the present invention, the term sinusoidal waveform as used herein refers to a surface having a repetitive oscillation of rounded, non-flat curvature described by mathematical formulas incorporating trigonometric functions sine, cosine, tangent or exponential and power series functions. These mathematical formulas are used in computer aided design and computer aided manufacturing software to create texture surfaces using rapid prototyping, milling, electrical discharge machining or similar techniques to create a polymer or metal surface with the sinusoidal waveform texture features. The advantage of using mathematical formulas is that large numbers of rounded, non-flat features can be created rapidly in computer aided design and computer aided manufacturing software.

All references cited herein are hereby incorporated by reference in their entirety.

We claim:

1. A microstructured surface comprising:
a thin film substrate having a first side and a second side, wherein at least a portion of the thin film substrate comprises a hierarchical microstructure pattern disposed about the thin film substrate;
the hierarchical microstructure pattern comprising a first set of microstructures and a second set of microstructures, the second set of microstructures being smaller than the first set of microstructures, and wherein a plurality of the second set of microstructures is disposed on each of the first set of microstructures.

2. The microstructured surface of claim 1, wherein the hierarchical microstructure pattern further comprises a third set of microstructures, wherein the third set of microstructures is smaller than the second set of microstructures, and a plurality of the third set of microstructures is disposed on each of the plurality of the second set of microstructures.

3. The microstructured surface of claim 1, wherein the hierarchical microstructure pattern is disposed on the first side of the thin film substrate.

4. The microstructured surface of claim 3, wherein the hierarchical microstructure pattern is disposed on the second side of the thin film substrate.

5. The microstructured surface of claim 1, wherein the first set of microstructures are from 25 microns to 1000 microns in height, and the second set of microstructures are from 5 microns to 100 microns in height.

6. The microstructured surface of claim 5, wherein the third set of microstructures are from 1 micron to 10 microns in height.

7. The microstructured surface of claim 1, wherein the first set of microstructures are from 25 microns to 1000 microns in width, and the second set of microstructures are from 5 microns to 100 microns in width.

8. The microstructured surface of claim 7, wherein the third set of microstructures are from 1 micron to 10 microns in width.

9. The microstructured surface of claim 1, wherein the first set of microstructures have a pitch between adjacent microstructures of 100 microns to 1000 microns, and the second set of microstructures have a pitch between adjacent microstructures of 10 microns to 100 microns in width.

10. The microstructured surface of claim 9, wherein the third set of microstructures have a pitch from 1 micron to 10 microns in width.

11. The microstructured surface of claim 1, wherein the thin film substrate is a glove.

12. The microstructured surface of claim 1, wherein the microstructure pattern is configured to generate a Wenzel Cassie wetting state.

13. The microstructured surface of claim 1, wherein the microstructure pattern generates at least 76 gm/cm$^2$ of force as tested using the moist meat testing method.

14. The microstructured surface of claim 1, wherein the microstructure pattern generates at least 118 gm/cm$^2$ of force as tested using the moist meat testing method.

* * * * *